United States Patent [19]

Freeman

[11] Patent Number: 5,489,401
[45] Date of Patent: Feb. 6, 1996

[54] METHOD FOR ENTRAPMENT OF ACTIVE MATERIALS IN CHITOSAN

[75] Inventor: Amihay Freeman, Ben Shemen, Israel

[73] Assignee: Ramot University Authority for Applied Research & Industrial Development Ltd., Tel-Aviv, Israel

[21] Appl. No.: 269,087

[22] Filed: Jun. 30, 1994

Related U.S. Application Data

[63] Continuation of Ser. No. 978,820, Nov. 19, 1992, abandoned.

[30] Foreign Application Priority Data

Nov. 20, 1991 [IL] Israel ......................................... 100096

[51] Int. Cl.$^6$ .............................. A61K 9/50; A61K 9/66; B01J 13/20; C12N 11/10
[52] U.S. Cl. ........................... 264/4.3; 264/4.1; 424/455; 424/461; 424/493; 428/402.2; 435/178; 514/963; 514/965
[58] Field of Search .................. 264/4.1, 4.3; 428/402.2; 424/455, 461, 493; 435/178; 514/963, 965

[56] References Cited

U.S. PATENT DOCUMENTS

| | | | |
|---|---|---|---|
| 4,082,688 | 4/1978 | Egawa et al. | 264/4.3 |
| 4,334,027 | 6/1982 | Klein et al. | 435/178 |
| 4,647,536 | 3/1987 | Mosbach et al. | 435/178 X |
| 4,803,168 | 2/1989 | Jarvis, Jr. | 435/178 X |
| 4,808,707 | 2/1989 | Daly et al. | 424/461 X |
| 4,822,534 | 4/1989 | Lencki et al. | 264/4.3 |
| 4,895,724 | 1/1990 | Cardinal et al. | 424/493 X |

FOREIGN PATENT DOCUMENTS

| | | |
|---|---|---|
| 0034293 | 8/1981 | European Pat. Off. . |
| 0371408 | 6/1990 | European Pat. Off. . |
| 2835874 | 2/1980 | Germany . |
| 1020087 | 1/1989 | Japan .................................. 435/178 |
| 1256389 | 10/1989 | Japan .................................. 435/178 |
| WO-A-8303102 | 9/1983 | WIPO . |

OTHER PUBLICATIONS

Sandford et al., "Chitosan–A Natural, Cationic Biopolymer: Commercial Applications," in *Industrial Polysaccharides: Genetic Engineering, Structure/Property Relations and Applications*, M. Yalpani ed., pp. 363–376, 1987.

Klein et al., "Methods for the Immobilization of Microbial Cells," *Applied Biochemistry and Bioengineering*, 4: 11–51, 1983.

Vorlop et al., "Entrapment of Microbial Cells in Chitosan," *Methods in Enzym.*, 135: 259–269, 1987.

Allan et al., "The Fungicidal Effect of Chitosan on Fungi of Varying Cell Well Composition," *Exp. Mycology*, 3: 285–287, 1979.

Freeman et al., "The Effect of Water–miscible Solvents on the $\Delta^1$–dehydrogenase Activity of Free and PAAH–entrapped *Arthrobacter simplex*," *Appl. Microbiol. Biotechnol.*, 25: 495–501, 1987.

Granot et al., "Cosolvent Effect on $\Delta^1$–steroid–reductase Activity of Free and PAAH Entrapped *Mycobacterium* Sp. NRRL B–3805 Cells," *Appl. Microbiol. Biotechnol.*, 27: 457–463, 1988.

Wada et al., "Continuous Production of Ethanol in High Concentration Using Immobilized Growing Yeast Cells," *Eur. J. Appl. Microbiol. Biotechnol.*, 11: 67–71, 1981.

Silbiger et al., "Continuous Cell Immobilization In Crosslinked Polyacrylamide–Hydrazide Beads," *Biotech. Bioeng.*, 30: 675–680, 1987.

Pines et al., "Immobilization and Characterization of *Saccharomyces cerevisiae* in Crosslinked, Prepolymerized Polyacrylamide–Hydrazide," *Eur. J. Appl. Microbiol. Biotechnol.*, 16: 75–80, 1982.

Primary Examiner—Richard D. Lovering
Attorney, Agent, or Firm—Foley & Lardner

[57] ABSTRACT

Encapsulation of active materials in chitosan beads of uniform size and improved mechanical and chemical stability. The active material is suspended in an acidic aqueous solution of a chitosan having a molecular weight of less than 250,000, the suspension is added dropwise to a crosslinking solution of diphosphate and glyoxal hydrate and the resulting beads are cured. It is possible to coat the active material with oil prior to suspension.

16 Claims, 1 Drawing Sheet

METHOD FOR ENTRAPMENT OF ACTIVE MATERIALS IN CHITOSAN

This application is a continuation of application Ser. No. 07/978,820, filed Nov. 19, 1992 now abandoned.

FIELD OF THE INVENTION

The present invention is in the field of encapsulation and relates to a new process for entrapment of active materials such as microorganisms, pharmaceuticals, pesticides and the like in chitosan beads for repeated use or sustained release. The encapsulation method according to the present process is suitable, among others, for entrapment of enzyme systems and microorganisms.

REFERENCES

1. P. A. Sandford and G. P. Hutchings, in "Industrial Poly-saccharides: Genetic Engineering, Structure/Property Relations and Applications", M. Yalpani, Ed. pp. 363–376, Elsevier (1987).
2. *Methods in Enzymology*, 135–137 (1987).
3. J. Klein and F. Wagner, *Applied Biochemistry and Bioengineering*, 4, 12–51 (1983).
4. *Methods in Enzymology*, 135, 173–472 (1987).
5. K. D. Vorlop and J. Klein, *Methods in Enzymology*, 135, 259–268 (1987).
6. German Patent, DE 2 835 875.
7. German Patent, DE 2 835 874.
8. C. R. Allan and L. A. Hadurger, *Exp. Mycol.* 3, 285–289 (1979).
9. A. Freeman and M. D. Lilly, *Appl. Microbiol. Biotechnol.* 25, 495–501 (1987).
10. I. Granot, Y. Aharonowitz and A. Freeman, *App. Microbiol. Biotechnol.*, 27, 457–463 (1988).
11. M. Wada, J. Kato and I. Chibata, *Eur. J. App. Microbiol. Biotechnol.* 11, 67–71 (1981).
12. E. Silbiger and A. Freeman, *Biotechnology and Bioengineering*, 30, 675–680 (1987).
13. G. Pines and A. Freeman, *Eur. J. App. Microbiol.* 16, 75–80 (1982).

BACKGROUND OF THE INVENTION AND PRIOR ART

Chitosan is a high molecular weight linear polymer composed of 2-amino-2-deoxy-D-gluose obtained by deacetylation of chitin-nature's second most abundant polymer. The chitosan solution properties and solubility as well as its chemical and biological characteristics make it an attractive biopolymer for a variety of applications. Chitosan whose solubility is known to be pH dependent and which is a non-toxic, biodegradable polymer having chelation abilities and even some therapeutic properties, has been used before in cosmetics for both hair and skin care, in agriculture as a fertilizer, in pharmaceutical compositions as wound healing and as a drug delivery agent, and in biotechnology as a matrix for entrapment of enzymes and cells (ref. 1).

Enzyme and whole cell entrapment has been well recognized as an important tool for carrying out numerous biotransformations and biosynthetic processes (for comprehensive review see ref. 2). The entrapment of the biocatalyst offers reuse of catalytic systems in various reactor configurations in either continuous or repeated batch operations, with significantly improved operational stability.

Whole cell entrapment may be achieved via cell adsorption or binding onto the surface of an appropriate particulate support or by physical entrapment in hydrophylic gel beads (for review see refs. 3, 4). The most popular approach to entrap cells is gel entrapment, in which cells are suspended first in aqueous solution of a monomer or a prepolymer. Then the solution is gellified by physical or chemical change (e.g. cooling, pH change, introduction of polymerization initiator or crosslinking agent), thus physically entrapping the cells.

Polysaccharides of biological origin (cog. alginate, carrageenan and agarose) are the most common matrices for cell entrapment. In recent years more attention has been focused on the potential of using chitosan as a matrix for entrapment of enzyme systems and cells due to several of its unique characteristics. The use of chitosan for this purpose is based on the fact that it is soluble in aqueous solutions of organic acids but readily precipitates upon elevation of the pH above 6 or by addition of anions such as pyrophosphate, alginate and lauryl sulfate (ref. 5). Using this dependency the following procedure was developed to prepare gel matrices for entrapment of cells: the cells to be entrapped were suspended in an aqueous organic acid solution of chitosan (pH<6), and the suspension was added dropwise into a precipitating solution containing pyrophosphate or alginate (refs. 5 to 7). The use of a precipitation solution containing high-molecular-weight counterions such as alginate, results in capsules while the use of low-molecular-weight counterions such as pyrophosphates affords millimeter size beads. The so-obtained bead shaped chitosan matrices are advantageous over gel matrices obtained with other polysaccharides because of their stability in the presence of phosphate buffers which is required in many processes involving enzymes and cells. In addition, chitosan matrices are stable to $Na^+$ and $K^+$ ions and are easily prepared at room temperature.

However, the use of chitosan has also some intrinsic drawbacks. Thus, for entrapment of biologically and chemically active materials one has to suspend the active material in an acidic solution which may damage pH sensitive materials such as cells or enzymes. Also, in many cases chitosan induces flocculation of cells (ref. 5). Chitosan has, moreover, antifungal activity which prevents its use for the entrapment of yeast cells (ref. 8).

Moreover, known methods for the encapsulation of active material in chitosan beads are based on a reversible gelation mechanism which results in beads with a relatively low mechanical and chemical stability. Therefore, entrapment of biologically and chemically active materials in chitosan beads are still limited (ref. 1).

It is the object of the present invention to provide an improved process for the entrapment of active materials in chitosan beads that have improved mechanical and chemical stability. It is a further object of the invention to provide a method by which pH sensitive active materials and active materials that are sensitive to contact with chitosan are adequately protected.

SUMMARY OF THE INVENTION

The process of the present invention is based on the observation that the addition of a suspension of an active material in an aqueous solution of chitosan containing small amount of organic acid to a crosslinking solution containing diphosphate buffer and glyoxal hydrate, brings about the instantaneous formation of uniform beads entrapping said active material and having improved mechanical and chemical properties.

Accordingly, the present invention provides a process for the encapsulation of at least one active material in chitosan beads, comprising:

(i) suspending said at least one active material in an acidic aqueous solution of chitosan of molecular weight less than 250,000;

(ii) adding the resulting suspension dropwise to a crosslinking solution containing 0.5–2% (w/v) of diphosphate and 1–4% (w/v) glyoxal hydrate whereby chitosan beads are formed with said at least one active material entrapped therein; and (iii) curing the resulting beads in the said crosslinking solution.

Typically, curing of the beads is performed at a temperature of 4° C. to 37° C.

If desired, the active material to be entrapped may be premixed with oil prior to its suspension in the said acidic aqueous solution of chitosan. In this way the active material is oil coated and direct contact between the active material and the acidic chitosan solution is avoided, which is particularly desirable when the active material is pH sensitive or chitosan sensitive.

Beads in which the entrapped active material is temperature sensitive may be washed with diphosphate buffer and stored in the cold until use.

Preferably the molecular weight of the chitosan used in accordance with the invention is within the range of about 60,000 to about 200,000 and its concentration in said acidic aqueous solution is typically about 1 to 5% (w/v), a preferred range of concentration being 2 to 3% (w/v).

In accordance with one embodiment of the invention, the said acidic aqueous solution of chitosan contains acetic acid. As a rule, the amount of acetic acid in this embodiment is less than 3% (v/v) and preferably about 11 % (v/v).

The crosslinking solution used in the performance of the encapsulation process according to the invention contains preferably about 1% (w/v) of diphosphate buffer, pH 7.0–8.5, and about 2 to 3% (w/v) of glyoxal hydrate.

In the performance of the process according to the invention the chitosan may, if desired, be sterilized prior to use.

Also if desired, the said at least one active material is added to said acidic aqueous chitosan solution in the form of a homogenized suspension.

The encapsulating beads prepared according to the present invention may be reinforced by a second incubation in a crosslinking solution which contains a complementary crosslinking agent such as glutaraldehyde, in phosphate buffer, e.g. a phosphate buffer solution containing an amount of up to 2% (v/v) and preferably about 0.5% (v/v) of glutaraldehyde. The reinforcement of the encapsulating beads by means of a second incubation in a crosslinking solution is particularly desired in cases where the entrapped active material is enzymes or cells that were precoated with oil.

If desired, the product beads may be washed with diphosphate buffer, typically with a 2% (w/v) solution, pH 8.0.

The encapsulating beads obtained by the process of the present invention are relatively uniform in size and shape, which is due to their fast formation. The increased mechanical and chemical stability of these beads is, inter alia, due to the fact that the crosslinking process involves a covalent chemical bonding.

Using the process of the present invention, a wide range of active materials can be entrapped. The relatively moderate pH of the chitosan solution and, where necessary, the oil-precoating of the active material to be entrapped prevent any undesired effects of the acidic solution and/or of the chitosan on the active material. Examples of such undesired effects are flocculation of cells and damage to cell walls when yeast or fungi are being entrapped. The precoating of the active material with oil does in some cases also promote the suspension of the active material.

DESCRIPTION OF THE DRAWINGS

In the following Examples results achieved with active material encapsulated in accordance with the invention, will be described with reference to the annexed drawings in which.

Figure 1:
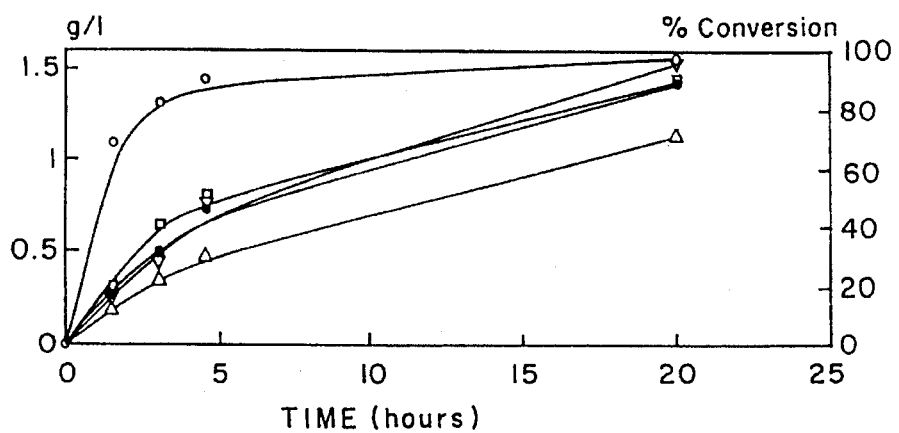
FIG. 1 is a graph showing the conversion of hydrocortisone to prednisolone by freely suspended *Arthrobacter simplex* cells and by cells entrapped in chitosan beads prepared according to Example 1.

The invention will now be illustrated by the following Examples, to which it is not limited.

EXAMPLE 1—Preparation of chitosan beads entrapping Arthrobacter simplex cells a. 1. Cell growth

Arthrobacter simplex (ATCC 6946) cells were grown, induced and harvested as described in ref. 9. The cells were frozen in liquid nitrogen and stored at −20° C. until used.

2. Cell suspension

Prior to use, 100 mg (20 mg dry cell weight) of frozen cells were transferred to ice cold 0.05 M tris, pH 7.8, and magnetically stirred over ice for 30 min. The suspension was then homogenized by a TEFLON glass homogenizer to ensure the formation of a uniform suspension.

b. Entrapment of *Arthrobacter simplex* cells in chitosan beads

Chitosan solution was prepared by suspending 3 g of chitosan of molecular weight of about 70,000 (Fluka) in 99 ml of water. One ml of glacial acetic acid was added and the suspension stirred magnetically overnight. The solution thus obtained was autoclaved (15 min. at 121° C.) and filtered to remove undissolved material.

Four *Arthrobacter simplex* samples were prepared by mixing 1 ml of the cell suspension obtained as described above with one of the following:

(1) 0.5 ml of 1 M tris pH 7.8, (2) 0.5 ml of 1 M tris in 2% chitosan, (3) 0.5 ml of tris (0.1 M, pH 7.8) containing 0.5% (v/v) Tween 80™; and (4) 0.5 ml of Tween 80™.

Each of these four samples were finely homogenized and added to 10 ml of acidic aqueous solution of chitosan. Following mixing by magnetic stirring, the suspension was pumped through a stainless steel tube (1 mm in diameter) at a flow rate of 3 ml/min to generate droplets which were dropped into 50 ml of 1% (w/v) diphosphate buffer (pH 8.2) containing 2% (w/v) glyoxal hydrate (Merck). Following incubation for 30 min in the crosslinking solution, the beads were separated by filtration.

The use and advantages of the above beads was demonstrated by the conversion of hydrocortisone into prednisolone. Beads obtained as described above were equilibrated twice with ice cold 1.6 mg/ml hydrocortisone (Sigma) solution in 0.05 M tris buffer pH 7.8 containing 5% (v/v) triethylene glycol. The beads were then incubated in the same substrate solution (final volume 50 ml) to which 0.8 ml of 0.5 M aqueous solution of menadione sodium bisulfite (Sigma) was added. The whole mixture was then incubated in 125 ml erlenmeyer flask in a gyratory shaker (100 rpm, 30° C.). Samples (0.3 ml) were removed periodically for analysis. The substrate and product were extracted by dichloromethane and analysed by HPLC according to ref. 9. FIG. 1 shows the conversion of hydrocortisone to prednisolone by freely suspended *Arthrobacter Simplex* cells (○) and by the four different chitosan beads prepared as described above.

The hydrocortisone dehydrogenation by the cells entrapped in the different chitosan beads was slower than that observed for freely suspended cells but nearly identical conversion levels were finally achieved after 20 hours with three out of four bead preparations (FIG. 1). In the first three bead preparations conversions of 90% to 98% of that obtained with freely suspended cells were obtained while in the fourth beads preparation the conversion was around 70% of that obtained with the freely suspended cells.

EXAMPLE 2—Preparation of chitosan beads entrapping *Bacillus megateriumcelis* a. Cell growth

*Bacillus megaterium* (ATCC 13368) cells were grown in growth medium prepared from extract mixture obtained from 40 g Bacto yeast and 16 g of Bacto soybean dissolved in one liter (pH 7.2). The cells were grown in 250 ml erlenmeyer flask (36 ml per flask, 200 rpm, 30° C.), until stationary phase (17 hrs, OD 660=8.5) was achieved. Cells were collected by centrifugation (10,000 g, 10 min) washed twice with 40 ml of phosphate buffer (0.2 M, pH 7.4) and centrifuged again.

b. Entrapment of cells in chitosan beads

The cell pellets thus obtained were mixed with protective medium of 0.5 ml of castor oil containing 5% (v/v) Tween 80™, or 0.5 ml saline (0.9%) containing 0.5% (v/v) acetic acid and 50 mM calcium chloride, of pH 5, and added into 20 ml of 3% chitosan solution prepared as described in example 1. Following homogenisation by means of magnetic stirring, the cell suspension was pumped at a rate of 3 ml/min through a stainless steel tube of 1 mm in diameter (ref. 9) to generate droplets which were laid into the crosslinking solution prepared as described in Example 1 and then incubated for curing and separated by filtration.

The use and advantages of the above beads was demonstrated by the hydroxylation of AD (4-androstene-3,17-dione). Beads containing entrappeal cells obtained as above were equilibrated twice with cold solution of 0.05 mg/ml AD in phosphate buffer (0.2 M, pH 7.4, 50 ml) and then assayed in 50 ml of the above mentioned substrate solution, in 250 ml erlenmeyer flask on a gyratory shaker (100 rpm, 30° C.). Samples were removed periodically and assayed by HPLC according to ref. 10.

Figure 2:
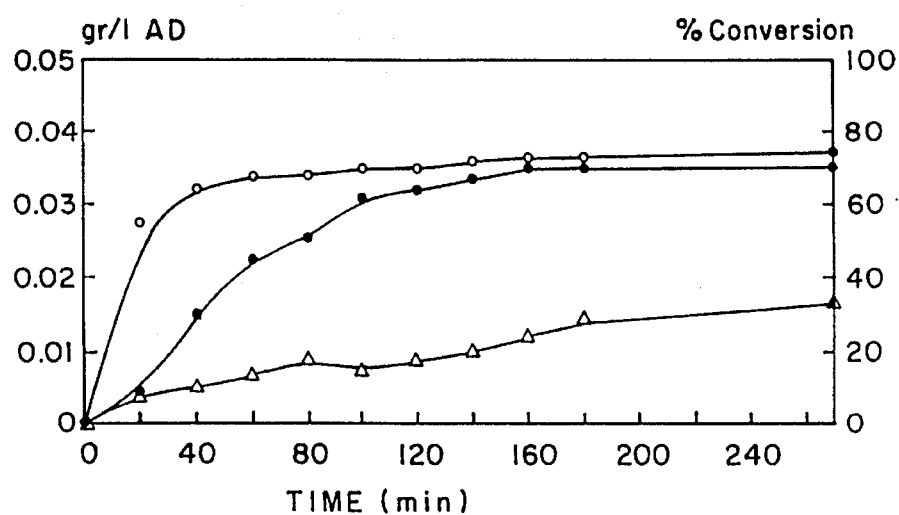
FIG. 2 is a graph showing the hydroxylation of AD (4-androstene-3, 17-dione) by freely suspended *Bacillus megaterium* cells and by cells entrapped in chitosan beads prepared according to Example 2.

FIG. 2 shows the conversion of AD (4-androstene-3,17-dione) by freely suspended (●) and two chitosan entrappeal *Bacillus megaterium* cells bead preparations (see (○) and (Δ) in FIG. 2). In those bead preparations the cells were treated prior to their suspension in the chitosan solution with 0.9% saline containing acetic acid (1% (v/v)) and calcium dichloride (0.1 M) or with castor oil containing 5% (v/v) Tween 80™. The results show that beads which contained cells prepared by promixing with castor oil as a protective agent exhibited a better activity and the conversion rate there was faster than in the corresponding freely suspended cell control (compare (●) with (○) in FIG. 2). Cells entrappeal in beads prepared with saline mixture containing calcium chloride (0.1 M) gave a lower conversion rate (see (Δ) in FIG. 2), while cells entrappeal in beads prepared by direct mixing of cells with chitosan solution had no activity at all (results not shown in FIG. 2).

EXAMPLE 3—Preparation of chitosan beads entrapping *Saccharomyces cerevisiae* (Bakers' yeast)

a. Cells

*Saccharomyces cerevisiae* cells were obtained from "Paka Industries Ltd.", Bat Yam, Israel. This product contained 30% (w/v) dry matter.

b. Entrapment of cells in chitosan beads 0.5 g (w/w) samples of yeast were mixed with 0.0, 0.3, 0.5, 0.75, and 1.0 ml castor oil containing 5% (v/v) Tween 80™, until fine pastes were obtained. These pastes were each mixed with 11 ml of 3% chitosan solution (prepared as described in Example 1) and beads were prepared as described in Example 1.

The use of the above beads was demonstrated by conversion of glucose into ethanol. Beads prepared as above were placed in an erlenmeyer flask (125 ml) and covered with a minimal amount of glucose (10% w/v. medium), prepared after ref. 11. The flasks were incubated at 30° C. on a gyratory shaker (80 rpm) overnight. The beads were then washed with citrate buffer (0.3% (w/v), pH5) and incubated in fresh glucose medium (50 ml) at 30° C. on a linear shaker (100 spm). Samples were removed periodically and ethanol analysis was carried out by GC according to ref. 12. The amount of ethanol (%, v/v) detected in the above mentioned entrapped yeast bead preparates was 0.0, 1.0, 1.5, 2.7, 2.3 respectively. These results clearly demonstrate that premixing of the yeast to be entrapped with castor oil maintained their activity and viability.

Glutardialdehyde is very toxic to baker's yeast and short exposure of these cells to glutardialdehyde without protection results in total loss of their glycolitic activity (13). Therefore, for further testing yeasts entrapped in beads prepared after premixing with castor oil (0.7 ml per 0.5 g yeast) were treated with cold 0.5% (w/v) glutardialdehyde solution in phosphate buffer (0.1 M, pH 8) for 30 min. The beads were washed with citrate buffer, incubated in a fresh glucose medium and tested for glycolytic activity as described above. Ethanol level of 2.5% (v/v) was detected demonstrating that these yeasts retained their glycolitic activity.

EXAMPLE 4—Preparation of chitosan beads entrapping benzaldehyde

Benzaldehyde (redistilled, Aldrich; 0.1 ml) was dissolved in 2.0 ml of castor oil and emulsified by magnetic stirring in 8 ml of 3% chitosan solution prepared as described in Example 1. Beads were prepared as described in Example 1.

Figure 3:
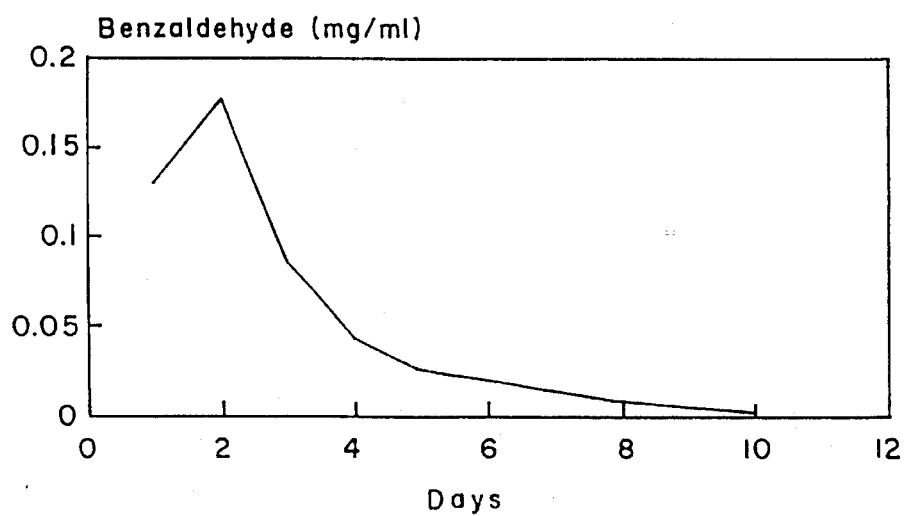
FIG. 3 is a graph showing the amount and rate of benzaldehyde release encapsulated in chitosan beads, according to Example 4.

The so prepared beads are suitable for sustained release of the entrapped benzaldehyde which was demonstrated by the following experiment. The beads were filtered and transferred into a 100 ml of phosphate buffer (50 mM, pH 7.5), and incubated at room temperature for 24 hours. The medium was then replaced daily and the benzaldehyde content was determined by HPLC under the conditions described for AD determination (ref. 10). The results are shown in FIG. 3.

Initial burst followed by gradual release of benzaldehyde into the daily exchanged medium was obtained for more than a week, proving the ability of said beads to be used as a sustained release delivery system.

I claim:

1. A process for the encapsulation of at least one active material in chitosan beads, comprising adding dropwise, a suspension of at least one active material in an acidic aqueous solution containing from about 2% to about 3% (w/v) of chitosan of molecular weight less than 250,000, to a crosslinking solution containing a 0.5–2% (w/v) of diphosphate buffer and 1–4% (w/v) glyoxal hydrate, whereby chitosan beads are formed with said at least one active material entrapped therein, and the formed beads are cured in said crosslinking solution.

2. A process according to claim 1, wherein the active material to be entrapped is premixed with oil before suspending it in the said chitosan solution.

3. A process according to claim 2, wherein the oil used for premixing the active material is castor oil.

4. A process according to claim 1, wherein the chitosan molecular weight is in the range of from about 60,000 to about 200,000.

5. A process according to claim 1, wherein the chitosan is dissolved in an aqueous acetic acid solution.

6. A process according to claim 5, wherein the concentration of acetic acid in the aqueous solution is less than 3% (v/v).

7. A process according to claim 6, wherein the concentration of acetic acid in the aqueous solution is about 1% (v/v).

8. A process according to claim 1, wherein the chitosan is sterilised prior to its use.

9. A process according to claim 1, wherein the said crosslinking solution contains about 1% (w/v) diphosphate buffer and about 2–3% (w/v) of glyoxal hydrate, whereby the pH of the crosslinking solution is about 7.0–8.5.

10. A process according to claim 1, wherein the curing of the formed beads is performed at a temperature between 4°–37° C.

11. A process according to claim 1, wherein the cured beads are washed with a 2% (w/v) diphosphate buffer solution, pH 8.

12. A process according to claim 1, wherein the beads obtained are subjected to a second incubation in a solution of a phosphate buffer containing a complementary crosslinking agent.

13. A process according to claim 12 wherein the complementary crosslinking agent is glutaraldehyde.

14. A process according to claim 13 wherein the concentration of glutaraldehyde does not exceed 2% (v/v).

15. A process according to claim 14 wherein the concentration of glutaraldehyde is about 0.5% (v/v).

16. A process according to claim 1, wherein said at least one active material is added to said acidic aqueous chitosan solution in the form of a homogenized suspension.

* * * * *